United States Patent [19]

Rha et al.

[11] Patent Number: 4,744,933
[45] Date of Patent: May 17, 1988

[54] PROCESS FOR ENCAPSULATION AND ENCAPSULATED ACTIVE MATERIAL SYSTEM

[75] Inventors: ChoKyun Rha, Boston; Dolores Rodriguez-Sanchez, Cambridge, both of Mass.

[73] Assignee: Massachusetts Institute of Technology, Cambridge, Mass.

[21] Appl. No.: 766,214

[22] Filed: Aug. 16, 1985

Related U.S. Application Data

[63] Continuation of Ser. No. 580,394, Feb. 15, 1984, abandoned.

[51] Int. Cl.$^4$ .......................... A61K 9/62; A61K 9/64; A61K 37/00; B01J 13/02
[52] U.S. Cl. ........................................ 264/4.3; 264/4.1; 424/93; 424/455; 424/460; 424/461; 428/402.2; 514/963
[58] Field of Search .................................. 264/4.1, 4.3; 428/402.2; 424/33, 455, 460, 461

[56] References Cited

U.S. PATENT DOCUMENTS

| | | | |
|---|---|---|---|
| 2,800,457 | 7/1957 | Green et al. | 428/402.2 |
| 3,415,758 | 12/1968 | Powell et al. | 428/404.2 X |
| 3,549,555 | 12/1970 | Hiestand et al. | 264/4.3 X |
| 3,629,392 | 12/1971 | Banker et al. | 424/33 X |
| 3,959,457 | 5/1976 | Speaker et al. | 424/35 X |
| 3,994,827 | 11/1976 | Sakai et al. | 264/4.1 X |
| 4,001,480 | 1/1977 | Shank | 264/4.1 X |
| 4,389,330 | 6/1983 | Tice et al. | 264/4.1 X |
| 4,391,909 | 7/1983 | Lim | 424/34 X |
| 4,407,957 | 10/1983 | Lim | 264/4.3 X |

*Primary Examiner*—Richard D. Lovering
*Attorney, Agent, or Firm*—Paul J. Cook

[57] ABSTRACT

Capsules are formed herein a liquified core while avoiding capsule core gelation by adding drops of a solution of either an anionic polymer composition or a cationic polymer composition to a solution of an ionic polymer of opposite charge. The drops contain an active ingredient such as a cell or microorganism capable of producing a biologically active product or can contain a biological or chemical composition. The interface of the ionic polymers form a permeable membrane surrounding the liquid drops.

14 Claims, No Drawings

PROCESS FOR ENCAPSULATION AND ENCAPSULATED ACTIVE MATERIAL SYSTEM

BACKGROUND OF THE INVENTION

The Government has rights in this invention under Grant Number NA79AA-D-00101 from the United States Department of Commerce.

This is a continuation of co-pending application Ser. No. 580,394 filed on Feb. 5, 1984, now abandoned.

This invention relates to a process for encapsulating biologically active materials such as cells or tissues or biochemically or chemically active compositions and to the encapsulated system including the active materials.

In biochemical production and biotechnological applications, health and viability of active materials such as cells, microorganisms and the like, is important since these active materials are capable of producing biologically or biochemically active components that find a wide variety of use. For example, cells are capable of producing antibodies, hormones, lymphokines, antibiotics, interferons and other biochemicals or chemicals. Mammalian cell lines are grown by being surrounded by an aqueous medium containing a nutrient in order to promote the viability and growth of the cells and enables continued production of the desired microbiological or biological products. It has been proposed to utilize so-called microcarriers, which are beads having the appropriate charge and exchange capacity to promote the growth of the cells thereon in an efficient manner. The microcarriers themselves are maintained in an aqueous suspension containing the proper nutrient composition to promote cell growth and production of the desired microbiological product. Biological products which are shed or excreted from the cells become admixed with the aqueous suspending composition, which in many cases, is at very dilute concentrations. The subsequent recovery of the desired product is thereby rendered difficult and time consuming.

In order to overcome problems associated with microbiological product recovery, it has been proposed to encapsulate cells or microorganisms within a membrane which permits nutrients to be metabolized by the cell or microorganism while retaining the microbiological product produced by the cell or microorganism within the encapsulating membrane. Such processes are disclosed, for example, in U.S. Pat. Nos. 4,409,331 and 4,352,883. The semipermeable membrane surrounding the biologically-active material has a selected permeability so that substances having a certain molecular weight or below, are allowed to pass through the semipermeable membrane. By controlling the permeability of the membrane, and by having a knowledge of the approximate molecular size of the desired product, one can confine the product, within the space between the active material and the semi-permeable membrane. Unfortunately, the process described in U.S. Pat. No. 4,409,331 and 4,352,883 require that the membrane be formed from the surface of an initially formed solid gel bead. This requires that the interior of the bead be subsequently liquefied so that the diffusion of nutrient which is required by the microorganism or cell, will not be hindered thereby to promote formation of the desired microbiological product. Furthermore, liquefaction of the gel is highly desired so that the space between the semi-permeable membrane and the microorganism or cell is available for either cell production or products. Typically, these prior art membranes are formed from a cell suspension in alginate solution which is added dropwise to a calcium chloride aqueous solution, thereby to form solid gel beads. The beads then are washed with N-cyclohexylamine ethane sulfonic acid (CHES) and then washed subsequently with sodium chloride. Thereafter, a polylysine solution is added to form a polymer complex with a alginate surface. This surface then is washed with CHES/sodium chloride, subsequently with calcium chloride and then subsequently with sodium chloride. The membrane then is incubated and the gel within the membrane is subsequently liquefied by washing twice with sodium chloride, incubating, washing with sodium citrate and sodium chloride, washing with sodium chloride, and then a final wash. Obviously, such a process for forming encapsulated microbiologically active ingredients is time consuming and difficult and requires a high level of laboratory technique in order to successfully produce the encapsulated cell or microorganism suspended in a liquid medium. Furthermore, during these complicated, time-consuming steps, the viability, productivity or other characteristic of the cell may be altered.

It would be highly desirable to provide a means for encapsulating a microorganism or cell capable of producing a biologically active material which eliminates the necessity of liquefying a solid carrier in order to promote mass transfer into and out of the cell or microorganism. Furthermore, it would be desirable to provide such an encapsulating means which is capable of drastically reducing the number of steps needed to form the encapsulated cell or microorganism. In addition, it would be desirable to provide such an encapsulating means which permits the formation of a membrane capable of having a permeability over a wide range, which permits the isolation of selective separation of a wide variety of biologically or chemically active molecules.

SUMMARY OF THE INVENTION

In accordance with this invention, cells, microorganisms, or the like, capable of producing a biologically active composition or biochemicals such as enzymes or hormones or the like are or nonbiochemical compositions such as substrates, reactants or catalyst, as encapsulated by a polymer complex comprising the combination of an anionic polymer and a cationic polymer. The term "active material" is used herein to include cells, microorganisms or the like which produce a biologically active composition or a composition such as an enzyme, hormone, antibody, antibiotic, insecticide, catalyst, substrate or reactant or the like which active material is to be encapsulated in accordance with this invention. The active material is suspended in an aqueous solution of either one of the cationic polymer or the anionic polymer composition. The polymer composition containing the active material then is formed into liquid particles and is added to the other polymer such as in the form of drops from a capillary tube or a spray or the like to form capsules comprising a membrane surrounding a liquid core. The active material is housed within the interior of the membrane suspended in the liquid core. The capsules then are washed and ready to use or then can be stored in an appropriate medium until use. The permeability of the membrane is controlled by controlling concentration of the cationic and anionic polymers in the solution used in the preparation of the capsule, the pH of the aqueous solutions in which the cationic polymer or anionic polymer are prepared, the presence or absence of counter-ions in each solution, and the molecular weight of the anionic polymer and the cationic polymer as well as the selection of specific polymers.

The process of this invention eliminates the need for liquefying the core of the capsule containing the active ingredient and also eliminates the need for multiple washing steps with a variety of reagents which may adversely affect the biological, biochemical or chemical activity of the active ingredient to be encapsulated. In addition, the process of this invention is useful with a wide variety of biologically active molecules over a wide molecular type and weight range, since the permeability of the membrane formed around the capsule can be varied widely. Thus, it is possible to separate, isolate or selectively segregate biologically active compounds of varying nature by controlling the permeability of the membrane.

DESCRIPTION OF SPECIFIC EMBODIMENTS

In accordance with this invention, an active material comprising or being capable of producing biologically active compositions is encapsulated within a membrane capable of permitting transport of a variety of compounds such as a nutrient for a cell to the active material and capable of selectively containing, within the membrane, the compound produced. The active ingredient can be a cell, microorganism, tissues or chemical or biochemical reactants. Representative suitable cells include fused cells, e.g., hybridoma cells, or genetically modified cells produced by recombinant DNA technology and lymphocyte cells capable of producing antobodies or microorganisms for fermentation.

In addition, microorganisms such as bacteria, can be encapsulated in accordance with this invention. Furthermore, biologically active compositions such as enzymes, hormones, antibiotics antibodies or the like can be encapsulated so that they can be controllably released through the membrane or retained therein if desired. The encapsulated active ingredient is enclosed by the membrane, which also can contain an aqueous medium which includes nutrients for the active ingredient. The aqueous medium also is capable of dissolving or suspending the microbiologically active material produced by the active ingredient without degrading it. The permeability of the membrane is such as to permit passage of nutrients from a medium surrounding the membrane into the aqueous medium enclosed by the membrane, and so that the microbiologically active composition can be produced by the active ingredient.

The active ingredient first is suspended in an aqueous solution of either (a) one or more anionic polymers or (b) one or more cationic polymers. The anionic polymer or cationic polymers chosen is formed of molecularly repetitive segments linked together which here are either positively charged or negatively charged segments distributed along the chain or on substitutions distributed along the chain. The concentration of charged segments is such as to permit electrostatic interaction and entanglement of the polymers when they are contacted together thereby to form the membrane. The resultant suspension then is sprayed into or added dropwise or the like as liquid particles to the other polymer so that a membrane is formed at the interface between the anionic polymer and the cationic polymer. When the interface between the two oppositely charged polymers encloses the active ingredient, the active ingredient thereby becomes encapsulated. Representative suitable anionic polymer include alginate, corragenan hyaluronic acids, carboxymethylcellulose, xanthan, furcellaran and, sulfonated organic polymers, usually in salt form, e.g., sodium salt. Representative suitable cationic polymers include chitosan, polylysine, polyethylamine and polyvinylamines as well as other amine or imine containing polymer which is capable of coacting with an anionic polymer to form a membrane. The preferred anionic polymers are alginate, or corragenan. The preferred cationic polymers are chitosan, or polylysine. The droplets of the charged polymer containing the active ingredient can be regulated in order to regulate the size of the final encapsulated product. Typical encapsulated products have a size within the range of about 50 microns and 5000 microns. When cells are to be encapsulated, the capsule has a size which permits oxygen transfer to those cells that require oxygen for viability and has a size sufficiently small to afford efficient isolation of the desired cell product, typically between about 400 and 800 microns.

The permeability of the membrane formed by the interaction of the anionic polymer and the cationic polymer is controlled by controlling the relative concentration of the two oppositely charged polymers, their concentration in the individual aqueous media, the pH of each of the polymer solutions, the molecular weights of the polymers and presence or absence of counter-ions in either of the solutions. By the terms "counter-ions" is meant ions which interact with the charged portion of the polymer in order to reduce interaction of that polymer with the oppositely charged polymer. For example, calcium ion interacts with carboxyl ion on the anionic polymer. The calcium ion can be removed with phosphate ion. Increased polymer concentration usually results in decreased permeability. An increase in the pH of the anionic polymer composition results in increased concentration of hydrogen ion thereby to form reactive cations on the cationic polymers having amine or imine groups. The achievement of a membrane having a desired permeability can be determined by varying the process parameters and incorporating a mixture of compounds of anions molecular weight and size in the droplets or spray the aqueous medium outside the capsules thus produced can be assigned for the presence of these compounds so that the molecular weight/molecular size cut-off level of the membrane is thus determined.

This invention also provide capsules having a normal membrane structure having improved mechanical properties as compared to the capsules of the prior art. Membranes produced from a gel composition and which are subsequently liquified have reduced strength. This is due primarily to the fact that a large proportion of the polymer chains becomes oriented toward the interior of the capsule during gelation rather than in the plane of the membrane. During liquification of the gel, these portions of the polymer chain do not become reoriented into the plane of the membrane and therefore do not contribute to membrane strength. In contrast, in this invention, the ionic portions of the anionic and cationic polymers need not be encumbered with counter ions so that they are free to react with each other along the entire chain length where the different polymers come into reactive contact. By operating in this manner, larger chain lengths of the polymers are oriented in the plane of the membrane. In one particular aspect of this invention, it is possible to have the anions polymer oriented on the outside of the membrane rather than on the inside of the membrane. Thus, for example, alginate can comprise the outer membrane surface. The result is not possible with prior art processes since the alginate is required to form the initial gel bead. Thus, this invention provides the user with much greater flexibility in forming the capsule. In another particular aspect of this invention, multi-membrane walls can be formed thereby providing membranes with greater strength as compared to capsule of the prior art. This is accomplished by forming the capsule with the anionic polymer chain on the outside of the membrane by the process set forth above. The capsules then are separated from the surrounding aqueous medium by any convenient method such as filtration or centrifugation. The capsules then are mixed with a solution of anionic polymer and a crosslinking divalent metal ion. For example, in the case of alginate as the anionic polymer calcium ion or barium ion can be used as the crosslinking divalent ion to form an outer membrane of alginate polymer.

After the encapsulated active ingredients are produced in accordance with the above-described process, then they can be separated from the aqueous medium where they are suspended, and then reintroduced into an aqueous medium which contains the nutrients for the active ingredient, so that the microbiologically active compound can be produced. On the other hand, the nutrients can be added to the suspension of encapsulated active ingredients without prior separation thereof.

The following examples illustrate the present invention and are not intended to limited the same.

EXAMPLE I

An alginate solution comprises 0.75 percent-1 percent w/v sodium alginate and 150 mM NaCi was added dropwise to a chitosan solution. The chitosan solution comprised 0.05–0.10 gr/dl chitosan, 117 mM NaCL, 0.01M $CaCL_2$ and 0.01M HCl. The chitosan solution had a pH of 6.5. The alginate solution was added dropwise to the chitosan solution to form capsules which were incubated in the chitosan solution for about 1 minutes. Samples of the chitosan solution containing the capsules were separated by centrifugation or by filtration on a sintered glass filter, washed with water and transferred separately to a phosphate buffer solution, a saline solution, distilled water or a cell culture medium comprising Dulbecco's Modified Minimum Essential Medium 5% Fetal Calf Serum and 5% Calf Serum and were found to be suprisingly stable. In addition, the capsules were found to be able to sustain centrifugation at a level at least as high as about 2000 RPM for 10 minutes. In this example, it is preferred that the alginate solution have a viscosity higher than about 3.0 centistokes while a chitosan solution preferably has a viscosity of at least about 1.5 centistokes.

EXAMPLE II

Following the procedure of Example I, capsules were formed by adding a chitosan solution dropwise to an alginate solution. The chitosan solution comprised 1.5 percent w/v chitosan, 2.5 percent citric acid and 0.07M $CaCl_2$. The alginate solution comprised either 1.1 percent w/v sodium alginate and 0.5 percent sodium sulfate, or a solution comprising 1 percent w/v sodium alginate. As an Example I, the capsules were found to be stable and phosphate buffer, saline, water and cell culture medium, and were able to sustain centrifugation at a level of about 2000 r.p.m. for at least 10 minutes.

The core of the capsules is rendered more fluid-like and less solid-like by lowering the concentration of calcium chloride in th chitosan solution.

EXAMPLE III

Following the procedure of Example I, capsules were formed by adding chitosan solution dropwise in an alginate solution to obtain capsules with a liquid core. The chitosan solution utilized contained between 0.1 percent and 1.5 percent w/v chitosan, 0.05M NaCl and between 0.006M and 0.2M $CaCl2$ and a pH ranging between 5.5 and 6.6. The alginate solution ranged between 0.1 percent and 1.0 percent sodium alginate.

As in Examples I and II, the capsules produced were found to be stable in phosphate buffer, saline, water and in the cell culture medium. As shown in Table I, the rupture strength of the capsules produced by this invention can be increased by treating them with a divalent ion after they are formed. Alternatively, the divalent ion can be added with a ionic polymer with which it does not interact to form a gel. The diffusion properties can also be controlled by solution conditions which influence the molecular configuration or the charge density of the polymers. The rupture strength of various capsules made in accordance with the procedures set forth in Example III is shown in Table I.

TABLE 1

| \multicolumn{3}{l}{Effect of divalent cations on the rupture strength of the capsules} |||
|---|---|---|
| Cation | Capsule Preparation | Rupture Strength ($9/cm^2$) |
| $Ca^{+2}$ | 1.35% chitosan, 0.05 N in 0.5% alginate; no treatment of capsules | 8 |
| $Ca^{+2}$ | Prepared as above + treatment of capsules in 0.1 M $CaCl_2$ for 5 minutes | 743 |
| $Ba^{+2}$ | 1.35% chitosan, 0.05 M $BaCl_2$ dropped in 0.5% alginate; no further treatment | 696 |
| $Ba^{+2}$ | Prepared as above + treatment of capsules in 0.1 M $BaCl_2$ for 5 minutes | 1609 |

We claim:
1. A process for producing a capsule having an aqueous liquid core from ionic polymers while avoiding gelation of the core comprising the steps of:
   forming an aqueous non-gel liquid droplet from an aqueous solution of a first ionic polymer selected from the group consisting of at least one anionic polymer and at least one cationic polymer, said liquid droplet containing an active material suspended in said droplet; and
   contacting said aqueous non-gel droplet with an aqueous solution of at least one second ionic polymer, said second ionic polymer having an ionic charge opposite from said first ionic polymer whereby said first and second polymers interact with each other and wherein said first ionic polymer and said second ionic polymer are free to react with each other along the entire chain lengths of said polymers where said polymers come into reactive contact with each other to form a membrane encapsulating said non gel droplets and said active material or aqueous liquid core containing said active material, and said encapsulated non gel droplets being suspended in said aqueous solution of said second ionic polymer.

2. The process of claim 1 wherein said active material is a lymphocyte.

3. The process of claim 1 wherein said active material is a bacteria.

4. The process of claim 1 wherein said active material is a biologically active compound.

5. The process of claim 4 wherein said compound is an enzyme.

6. The process of claim 4 wherein said compound is a hormone.

7. The process of claim 1 wherein said active material is at least one living cell.

8. The process of claim 7 wherein said cell is a hybridoma.

9. The process of claim 1 wherein the said active material is a microorganism.

10. The process for producing a product for a living cell which comprises encapsulating said cell by the process of claim 1 and controlling the permeability of said membrane to prevent said product from permeating said membrane, collecting said encapsulated cell, rupturing said membrane and recovering said product.

11. The process of claim 10 wherein said cell is a hybridomia.

12. The process of claim 10 wherein said cell is a lymphocyte cell.

13. The process of any one of claims 1, 10, 11 or 12 wherein said anionic polymer is selected from the group consisting of alginate and carragenan.

14. The process of anyone of claims 1, 10, 11 or 12 wherein said cations polymer is selected from the group consisting of chitosan and polylysine.

* * * * *